US008165684B2

(12) United States Patent
Putz et al.

(10) Patent No.: US 8,165,684 B2
(45) Date of Patent: Apr. 24, 2012

(54) WIRELESS SYSTEM FOR EPILEPSY MONITORING AND MEASUREMENT

(75) Inventors: David A. Putz, Pewaukee, WI (US);
Bharat S. Joshi, Pineville, NC (US);
Bruce Lanning, Littleton, CO (US);
James A. Nolan, Lakewood, CO (US);
Gregory J. Nuebel, Bailey, CO (US);
Dennis D. Spencer, Woodbridge, CT (US); Hitten P. Zaveri, New Haven, CT (US)

(73) Assignee: Yale University, New Haven, CT (US)

( * ) Notice: Subject to any disclaimer, the term of this patent is extended or adjusted under 35 U.S.C. 154(b) by 500 days.

(21) Appl. No.: 12/184,663

(22) Filed: Aug. 1, 2008

(65) Prior Publication Data

US 2009/0149913 A1 Jun. 11, 2009

Related U.S. Application Data

(60) Provisional application No. 61/040,650, filed on Mar. 29, 2008, provisional application No. 60/963,012, filed on Aug. 1, 2007.

(51) Int. Cl.
*A61N 1/00* (2006.01)
*A61B 5/04* (2006.01)

(52) U.S. Cl. ............. 607/45; 607/33; 600/518; 600/544

(58) Field of Classification Search ................... 607/45, 607/33; 600/544, 518
See application file for complete search history.

(56) References Cited

U.S. PATENT DOCUMENTS

| 7,212,851 | B2 | 5/2007 | Donoghue et al. |
| 7,280,870 | B2 | 10/2007 | Nurmikko et al. |
| 7,346,312 | B2 | 3/2008 | Irazoqui-Pastor et al. |
| 2004/0133119 | A1* | 7/2004 | Osorio et al. ............... 600/544 |
| 2008/0208781 | A1* | 8/2008 | Snyder ............................ 706/20 |

OTHER PUBLICATIONS

Excerpts of International Search Report and Written Opinion for PCT/US08/009384. Date: Nov. 4, 2008. 4 pages.
Chow, Eric Y., "High Data-Rate Wireless Transcutaneous-Telemetry Using High-Frequency Asics for Neural Prostheses." Thesis, Masters of Science in Electrical and Computer Engineering, Purdue University, West Lafayette, IN. Date: May 2007.
Irazoqui-Pastor, Pedro, "Transcutaneous Inductively Powered Neural Recording System." Dissertation, Biomedical Engineering, University of California, Los Angeles, CA. Date: 2003.

(Continued)

*Primary Examiner* — Niketa Patel
*Assistant Examiner* — Nicole F Lavert
(74) *Attorney, Agent, or Firm* — Welsh Flaxman & Gitler LLC

(57) ABSTRACT

A wireless system for monitoring a patient's brain tissue including (1) a plurality of electrodes abutting brain tissue, (2) main circuitry outside the patient's body to transmit power at radio frequencies and send/receive data using infrared energy, and (3) subcutaneously-implanted remote circuitry connected to the electrodes and configured to (a) receive transmitted RF power, (b) capture and digitize EEG signals from the electrodes, and (c) send/receive data to/from the main circuitry using IR energy, including sending digitized EEG signals from each electrode to capture the full bandwidth of each EEG signal. The system preferably includes circuitry to measure the electrical impedance of each electrode for real-time monitoring of the condition of the electrode/tissue interfaces to enhance interpretation of captured EEG signals.

29 Claims, 15 Drawing Sheets

OTHER PUBLICATIONS

Hassell, Travis, J. et al., "Constant-Current Adjustable Waveform Microstimulator for an Implantable Bi-Modal Output Hybrid Neural Prosthesis." Date: Apr. 2, 2007.

Moriziio, J. et al., "Wireless Headstage for Neural Prosthetics." Triangle BioSystems, Inc., Durham, NC. Date: Mar. 2005.

Chow, Eric Y., et al., Miniature Antenna for RF Telemetry through Ocular Tissue. Department of Electrical and Computer Engineering, Purdue University, West Lafayette, IN. Date: Copyright 2008.

Patterson, William R., et al. "A Microelectrode/Microelectronic Hybrid Device for Brain Implantable Neuroprosthesis Applications." IEEE Transactions on Biomedical Engineering, No. 10, vol. 51. Date: Oct. 2004.

Song, Yoon-Kyu et al., "Development of a Chipscale Integrated Microelectrode/Microelectronic Device for Brain Implantable Neuroengineering Applications." IEEE Transactions on Neural Systems and rehabilitation Engineering, vol. 13, No. 2. Date: Jun. 2005.

Saito, Toshiyuki et al., "Radiotelemetry Recording of Electroencephalogram in Piglets During Rest." Physiology & Behavior, 84, pp. 725-731. Date: 2005.

Song, Yoon-Kyu et al., "A Brain Implantable Microsystem with Hybrid RF/IR Telemetry for Advanced Neuroengineering Applications." 29th Annual International Conference of the IEEE EMBS, Lyon, France. Date: Aug. 23-26, 2007.

Yun, Xiao et al., "Low-Power High-Resolution 32-Channel Neural Recording System." 29th Annual Conference of the IEEE EMBS, Lyon, France. Date: Aug. 23-26, 2007.

Murari, Kartikeya et al., "Wireless Multichannel Integrated Potentiostat for Distributed Neurotransmitter Sensing." Engineering in Medicine and Biology 27th Annual Conference, Shanghai, China. Date: Sep. 1-4, 2005.

Parthasarathy, Jayant et al., "Battery-Operated High-Bandwidth Multi-Channel Wireless Neural Recording System using 802.11b." 28th IEEE EMBS Annual International Conference, New York City, New York. Date: Aug. 30-Sep. 3, 2006.

Farshchi, Shahin et al., "A TinyOS-Enabled MICA2-Based Wireless Neural Interface." IEEE Transactions on Biomedical Engineering, vol. 53, No. 7. Date: Jul. 2006.

Farshchi, Shahin et al., "Bi-Fi: An Embedded Sensor/System Architecture for Remote Biological Monitoring." IEEE Transactions on Information Technology in Biomedicine, vol. 11, No. 6. Date: Nov. 2007.

Borghi, T. et al., "A Compact Multichannel System for Acquisition and Processing of Neural Signals." 29th Annual Conference of the IEEE EMBS, Lyon, France. Date: Aug. 23-26, 2007.

Chen, Hsin-Yung et al., "A Low Noise Remotely Controllable Wireless Telemetry System for Single-Unit Recording in Rats Navigating in a Vertical Maze." Med Biol Eng Comput, 46:833-839. Date: 2008.

* cited by examiner

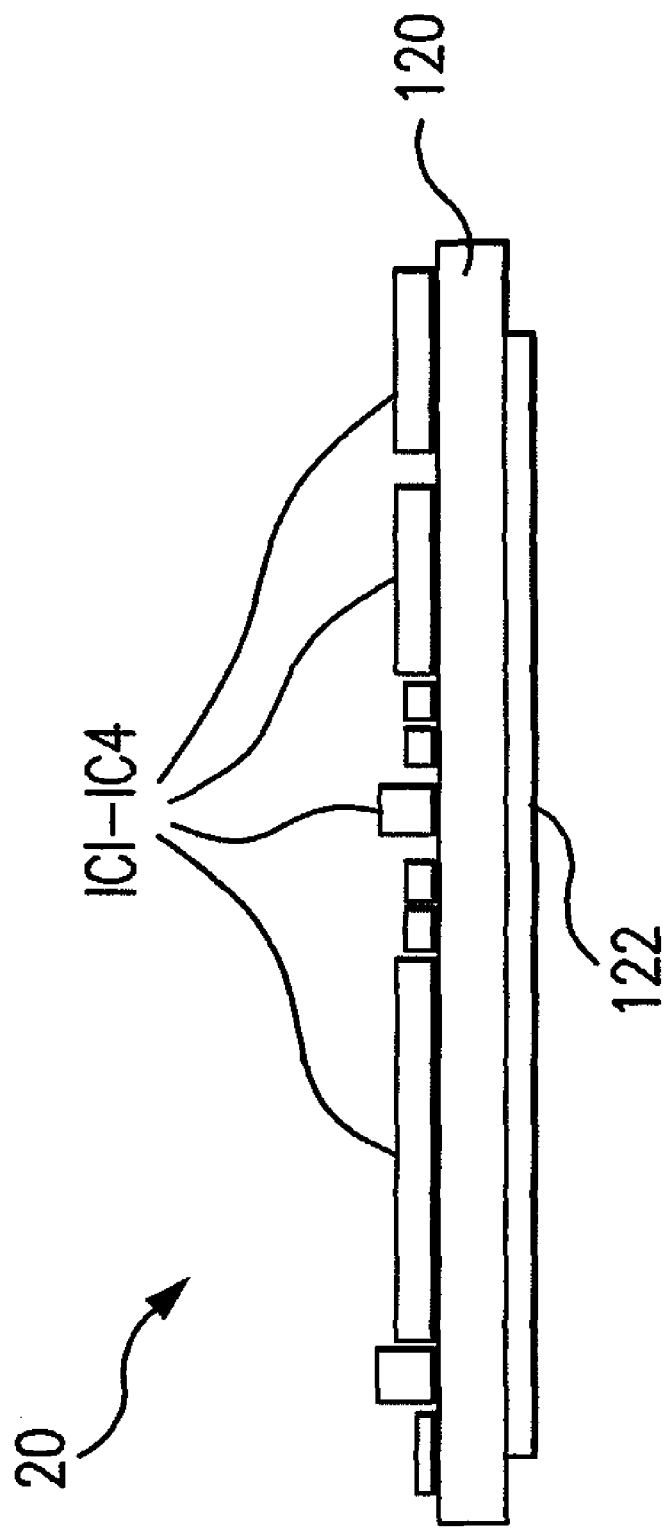

WIRELESS SYSTEM FOR EPILEPSY MONITORING AND MEASUREMENT

RELATED APPLICATIONS

This application claims the benefit of U.S. Provisional Patent Application Ser. No. 61/040,650, filed Mar. 29, 2008, and U.S. Provisional Patent Application No. 60/963,012, filed Aug. 1, 2007, the entire contents of which are incorporated herein by reference.

FIELD OF THE INVENTION

The invention relates generally to devices for monitoring and mapping of brain activity in epilepsy patients and patients with other neurological disorders and, more particularly, to systems which facilitate accurate measurement for periods of time through the use of implanted devices and electrodes.

BACKGROUND OF THE INVENTION

Accurate sensing of intracranial electrical activity, such as for determining epileptogenic foci or otherwise, often may require use of a plurality of brain contacts. Epileptogenic mapping is one example of the use of electrical devices with tissue-engagement contacts. Examples of two kinds of intracranial electrical contact devices are depth probes and flexible flat surface members.

Depth probes, which may be referred to as "depth electrodes," penetrate deep into the brain tissue. On the other hand, flexible flat surface members, including what are sometimes referred to as "strip" electrodes and "grid" electrodes, may be placed subdurally in direct contact with brain tissue at the surface of the brain.

Examples of such electrodes include but are not limited to electrodes described in U.S. Pat. No. 4,735,208 (Wyler et al.), U.S. Pat. No. 4,805,625 (Putz), U.S. Pat. No. 4,903,702 (Putz), U.S. Pat. No. 5,044,368 (Putz), and U.S. Pat. No. 5,097,835 (Putz).

Each of these different kinds of intracranial tissue-engagement electrodes are connected to some circuitry which typically captures and records the EEG signals for analysis of various types. There is a diagnostic need for an increased number of electrodes in order to increase the precision of analysis and diagnosis based on the captured EEG information. An increase in the number of electrodes requires higher data transmission bandwidths if the full amount of data captured from the electrodes is delivered to the monitoring system electronics. Further, there is a diagnostic need to monitor patients for longer periods of time, again for increased precision of diagnosis.

State-of-the-art monitoring systems in diagnostic use, or at least the great majority of such systems, today require a patient suffering from epilepsy to have at least one opening through the patient's skin during the entire period in which the electrodes are implanted for monitoring purposes. It is highly desirable medically, however, to avoid wires/devices through the skin to be in place during such monitoring, since any opening in the skin is an opportunity for infection to develop. Thus, it is highly desirable to avoid prolonged periods during which there are openings in the skin. Further, monitoring systems typically require that a patient be tethered by wires to the monitoring equipment. The existence of a tether is both interfering and inconvenient.

Monitoring systems with electrodes placed to abut brain tissue in various configurations can also be used to provide electrical stimulation of brain tissue as one mode of medical treatment. In making EEG measurements or delivering such electrical stimulation, there is a need to know over time what the condition of an implanted electrode is while it abuts brain tissue. An electrode may shift from its initial implanted position or lesions may form at an electrode, thereby changing conditions under which monitoring and/or stimulation occur in way which affects the degree of precision of such monitoring and/or stimulation. Knowing and reacting to the electrical impedance of implanted electrodes and to impedance changes would be important to assessment of the condition of an implanted electrode and to enhancing the precision of diagnosis and treatment. One aspect of the present invention provides such impedance-measuring capability.

In order to meet some of the above-mentioned needs, in particular the need to avoid openings in the skin for prolonged periods of time, it is desirable to implant not only the electrodes but also the circuitry which interfaces the electrodes with the remainder of the monitoring system. In order to accomplish this, power must be provided to such an implanted device. This creates a need for low power consumption and medically-safe approaches to providing power.

Power can be provided to an implanted device by either providing an onboard source of power such as a battery or by transmitting power to the implanted device. In the case of devices to which power is transmitted, there is a need to transmit power with as low power loss as possible in order to affect human tissue as little as possible. In the case of providing onboard power, there is a need for completely dry and fully-encased power sources.

Some wireless brain-interactive systems have previously been disclosed in the literature for various purposes, including for monitoring EEG signals in patients. Prior wireless systems for monitoring EEG signals in patients fall short of meeting the wide variety of needs which characterize the complex challenges facing the medical community in providing such diagnosis and treatment today.

Certain other wireless brain-interactive systems in the literature are directed toward providing a brain-machine interface to allow amputees to control prosthetic limbs, an entirely different than brain monitoring/mapping of neurological-disorder patients. Unlike monitoring/mapping systems, which seek to capture signals that are composites of the signals from a great many neurons, brain-machine interface systems are typically concerned with capturing signals from individual neurons. Significant differences exist in the nature of the electrodes of these two sorts of systems, as does the type of processing that would be required and the bandwidths involved. With regard to the electrodes, brain-machine interface systems have point-like brain-tissue contact, while monitoring/mapping systems employ surface contact, either involving flat disk surfaces or cylindrical surfaces. The present invention is in the specific field of monitoring/mapping systems.

The wireless system for monitoring/mapping brain tissue disclosed herein meets the complex set of needs in the monitoring/mapping field. Among the needs addressed are the need for an increased number of electrodes with all of the data available in the EEG signal at each electrode being captured with high precision in real-time and available for analysis, and the need to assess the condition of the implanted electrodes over time to assure proper capturing of EEG signals on the surface electrodes used.

OBJECTS OF THE INVENTION

It is an object of the invention, in the field of EEG monitoring, to provide a monitoring system which overcomes certain problems of the prior art, including those mentioned above.

Another object of the invention is to provide an improved system for monitoring brain tissue which eliminates openings in the skin for prolonged periods.

Another object of the invention is to provide an improved wireless system for monitoring brain tissue which enables the monitoring of a large number of implanted electrodes in order to increase the precision of the diagnostic information produced, thereby improving diagnostic accuracy.

Still another object of the invention is to provide an improved wireless system for monitoring brain tissue which captures and transmits the full amount of information contained in the EEG signals.

Yet another object of the invention is to provide an improved wireless system for monitoring brain tissue which consumes low power and can be physically small, thereby avoiding a large implanted device.

Another object of the invention is to provide an improved system for monitoring brain tissue without a tether to the patient.

Another object of the invention is to provide an improved wireless system for monitoring brain tissue which may operate without an implanted battery.

Another object of the invention is to provide an improved wireless system for monitoring brain tissue which may include a medically-safe battery for certain periods of operation.

Yet another object of the invention is to provide an improved wireless system for monitoring brain tissue which provides increased freedom for the monitored patient.

Still another object of the invention is to provide an improved wireless system for monitoring brain tissue which has low power losses within the skin tissue surrounding the implanted device.

Another object of the invention is to provide an improved system for monitoring brain tissue which provides measurements of implanted electrode electrical impedance in order to assess the condition of electrodes over time.

Another object of the invention is to provide an improved system for monitoring brain tissue which can be retained within a patient during an MRI procedure.

These and other objects of the invention will be apparent from the following descriptions and from the drawings.

SUMMARY OF THE INVENTION

The present invention is a wireless system for monitoring the brain tissue of a patient. The system comprises (1) a plurality of electrodes configured to abut brain tissue, (2) main circuitry for placement outside the body of the patient and configured to transmit power at radio frequencies and send and receive data using infrared energy, and (3) remote circuitry for subcutaneous implantation in the head of a patient, the remote circuitry being connected to the plurality of electrodes and configured to (a) receive transmitted power at radio frequencies from the main circuitry, (b) capture and digitize EEG signals from each of the electrodes, and (c) send data to and receive data from the main circuitry using infrared energy, including sending the digitized EEG signals from each of the electrodes sampled to capture the full bandwidth of each EEG signal.

In some preferred embodiments of the invention, the radio frequencies are in the range of between 13.55 MHz and 13.57 MHz. Also in some embodiments, each digital signal has a digital resolution of at least about 12-16 bits. In highly-preferred embodiments, the sampling occurs at least about 500 times per second.

In some preferred embodiments of the inventive wireless brain-monitoring system, the remote circuitry is further configured to measure the electrical impedance of each of the plurality of electrodes. Further, in some embodiments, the remote circuitry is further configured to send the impedance measurements to the main circuitry as digital signals.

Some embodiments of the inventive brain-monitoring system include a power storage capacitor in the remote circuitry to provide power when high current flow is required.

Further, some preferred embodiments of the brain-monitoring system include a battery as part of the remote circuitry to augment the RF-supplied power. In some highly-preferred embodiments, the battery is a solid-state lithium rechargeable battery.

In other preferred embodiments of the inventive wireless brain-monitoring system, the remote circuitry further includes at least one circuit-loop-interrupting element having an open state, thereby rendering the remote circuit MRI-safe when the at least one circuit-loop-interrupting element is in the open state.

Some other embodiments of the inventive system include a video camera and recording system to simultaneously record the EEG signals and video images of the patient.

Further, some preferred embodiments of the inventive system for monitoring the brain tissue of a patient are not wireless systems and comprise a plurality of electrodes configured to abut brain tissue and circuitry connected to the plurality of electrodes and configured to (a) capture EEG signals from the electrodes and (b) measure the electrical impedance of each of the plurality of electrodes, thereby to monitor the condition of the electrode/tissue interfaces to enable interpretation of captured EEG signals. Some of these preferred embodiments are further configured to provide electrical energy to at least one of the plurality of electrodes to stimulate brain tissue.

As used herein, the term "full bandwidth" means having a bandwidth which is wide enough to include the data contained in each of the monitored EEG electrodes, the data content including information at all frequencies up to, for example, at least 250 Hz or higher. When an analog signal contains frequencies up to a frequency $f_1$ cycles per second and such a signal is sampled to create a stream of digital signals, information theory requires that the sampling rate be at least $2 \cdot f_1$ times per second in order to retain all of the data contained in the analog signal. Further, if there are N such analog signals being sampled from, say, N electrodes, and each of such digital signals is represented by a digital signal using D bits per sample, then the minimum amount of data in a combined digital signal having "full bandwidth" is equal to $2 \cdot f_1 \cdot N \cdot D$ bits per second, assuming no extra bits of information are included in the signal. For example, the minimum "full bandwidth" of a combined digital signal in a system which has 256 electrodes and 16 bits per sample, sampled at 500 Hz is just over 2 Mbits per second.

As used herein, the word "abut" pertaining to the position of an electrode with respect to brain tissue refers to an electrode coming in contact with the brain tissue in any way, including being placed next to the tissue and being positioned to penetrate the tissue.

As used herein, the term "circuit-loop-interrupting element" means a device which breaks a circuit loop or places a suitably high impedance within a circuit loop such that little or no current will be induced to flow in the such loop during exposure to an MRI operating environment.

The term "MRI-safe" as used herein means the a device is configured to be present in an MRI operating environment (with the device not operating) without either damage occurring to the device or the tissue of the patient whose head contains the device. For example, a number of steps can be taken to render a electrical device MRI-safe. MRI-safe in the context of this document indicates that the step being indicated contributes to the MRI safety of the circuit, not that it alone renders the entire device MRI-safe.

BRIEF DESCRIPTION OF THE DRAWINGS

The drawings illustrate preferred embodiments which include the above-noted characteristics and features of the invention. The invention will be readily understood from the descriptions and drawings.

FIG. 9A also illustrates an infrared data link to a computer which communicates with the main circuitry over such a data link.

FIG. 11 is a schematic illustration of the inclusion of a solid-state lithium rechargeable battery in the packaging of the alternative embodiment of the remote circuitry of the inventive brain-monitoring system as shown in FIG. 10.

DETAILED DESCRIPTION OF PREFERRED EMBODIMENTS

Figure 1:
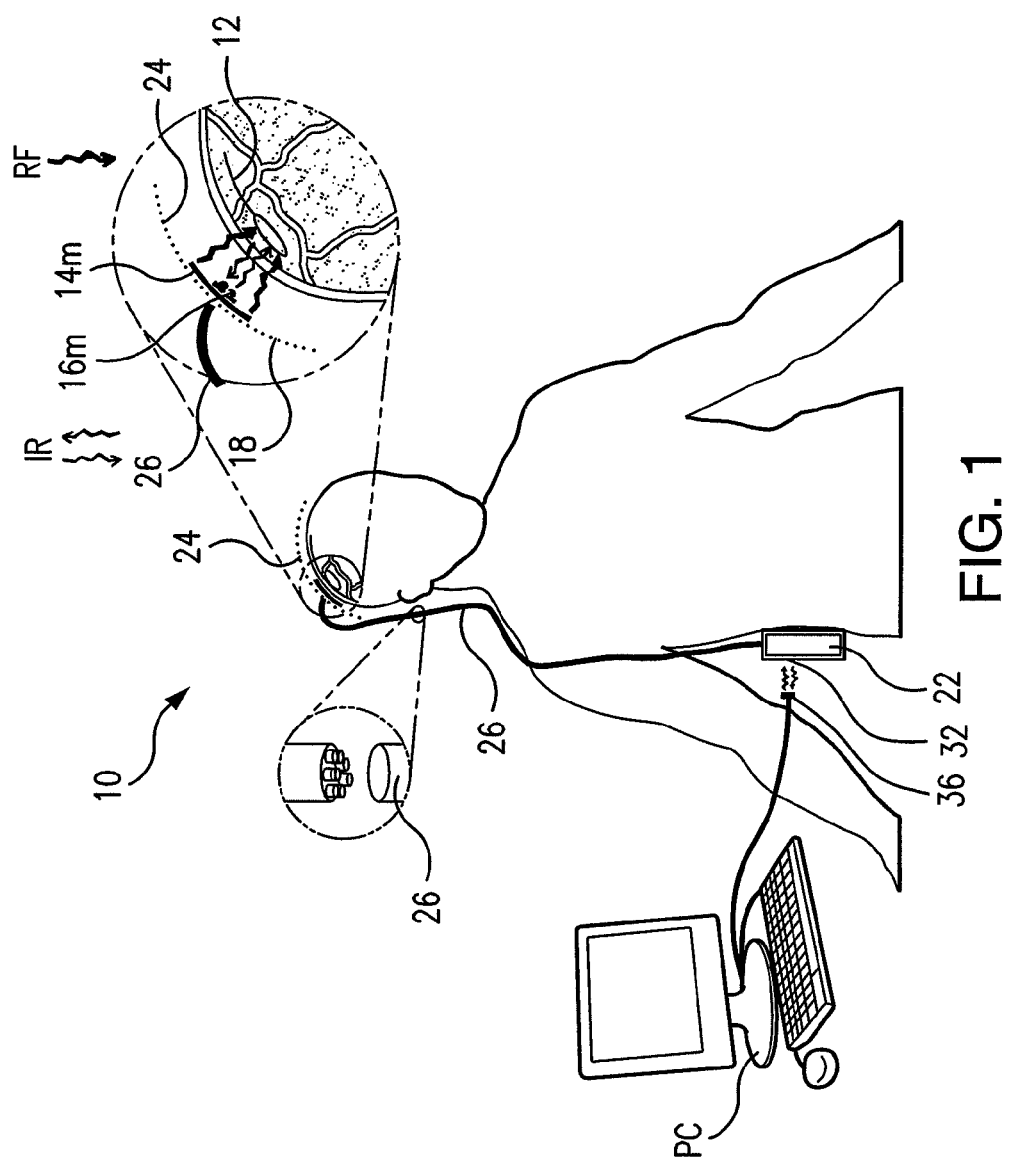
FIG. 1 is a schematic diagram of one embodiment of the inventive wireless system for monitoring the brain tissue of a patient.

FIG. 1 is a schematic diagram of one embodiment of the inventive wireless system for monitoring the brain tissue of a patient. A plurality of electrodes 12 are implanted in the human brain to abut brain tissue, and are positioned to monitor EEG signals where the physician performing the procedure determines are regions of interest within the patient's brain. (In this document, reference number 12 is used when referring to either a single selected electrode or the plurality of electrodes. In each case, the single/plural context is clear.) Electrodes 12 are connected to an implanted device containing remote circuitry 20. Included as part of remote circuitry 20 is an RF inductive receive coil 14r connected to TP1 and TP2 in FIGS. 4 and 10. One embodiment of coil inductive receive coil 14r is shown in FIG. 4A. Also included in remote circuitry 20 is an infrared transceiver 16r (shown in FIG. 6) for transmitting and receiving data with an infrared signal across the skin 18 of the patient being monitored. IR transceiver 16r is aligned with a hole in the patient's skull in order to transmit and receive IR signals through skin 18.

Figure 9:
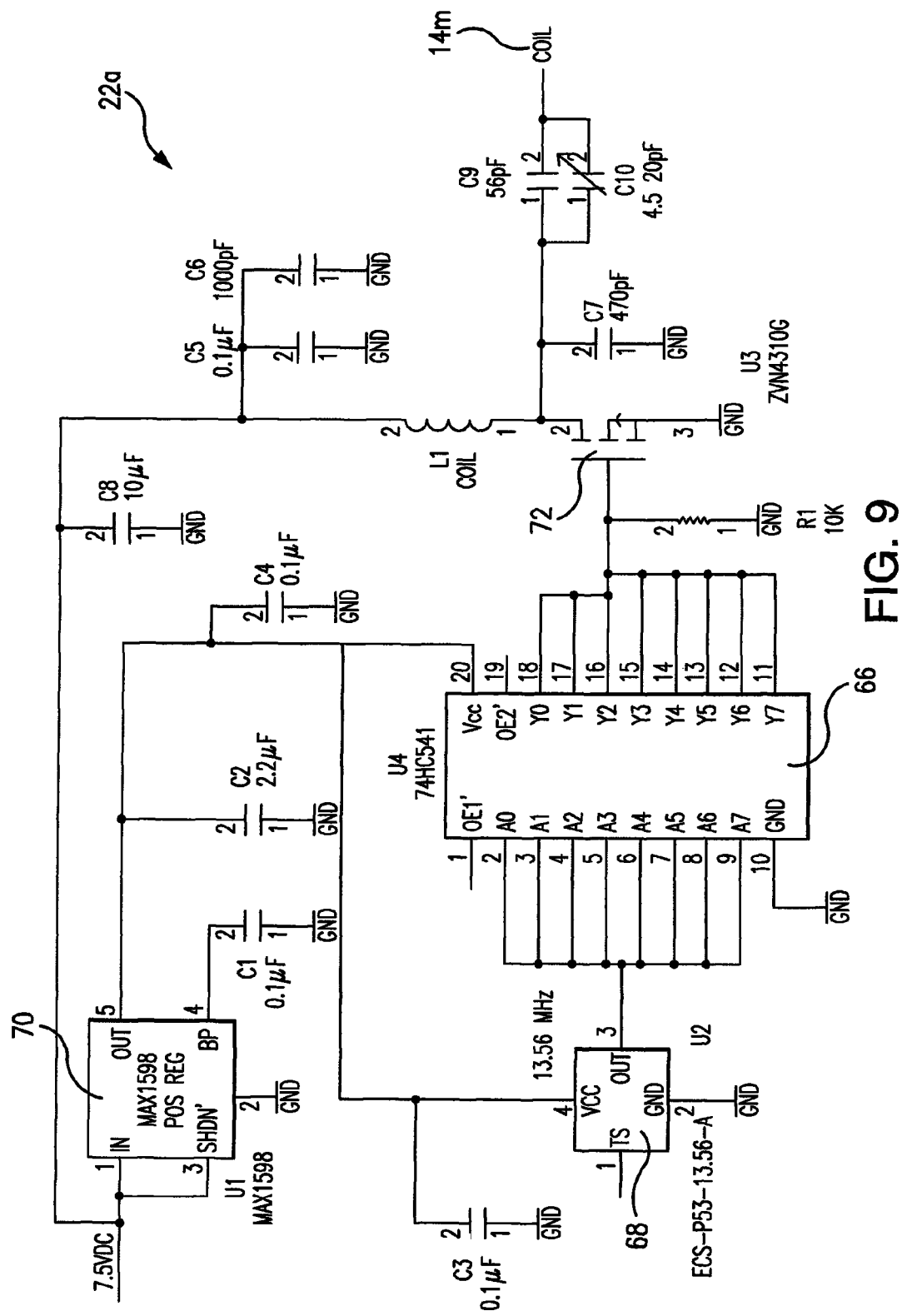
FIG. 9 is a circuit diagram of a portion of the main circuitry of the inventive brain-monitoring system of FIG. 1, illustrating an embodiment of the RF power amplifier therein.

Wireless monitoring system 10 also includes main circuitry 22 (also shown in FIG. 9). Main circuitry 22 includes an RF inductive transmit coil 14m to transmit power to remote circuitry 20 and an IR transceiver 16m to receive data from and send data to remote circuitry 20. Both inductive transmit coil 14m and transceiver 16m are located at the end of suitable cabling 26 to main circuitry 22 such that these elements can be conveniently positioned with respect to the head of the patient being monitored.

RF inductive receive coil 14r within remote circuitry 20 receives power from an RF inductive transmit coil 14m which is part of main circuitry 22. FIG. 1 shows one embodiment of how inductive transmit coil 14m may be positioned to transmit power to remote circuitry 20 through skin 18, using a flexible cap 24 to hold inductive transmit coil 14m and IR transceiver 16m in place.

As shown in FIG. 1, main circuitry 22 may be interfaced with a computer (labeled PC) through the use of an IR transceiver 32 connected to a serial port on main circuitry 22. IR transceiver 32 communicates with a similar dongle 36 connected with a serial port on the computer (PC). Such IR transceiver dongle devices are well-known to those skilled in the art, and further details are not included in this document on IR transceiver 36. There are other ways in which data received from remote circuitry 20 can be handled and the embodiments shown herein are not intended to be limiting in any way.

Figure 2:
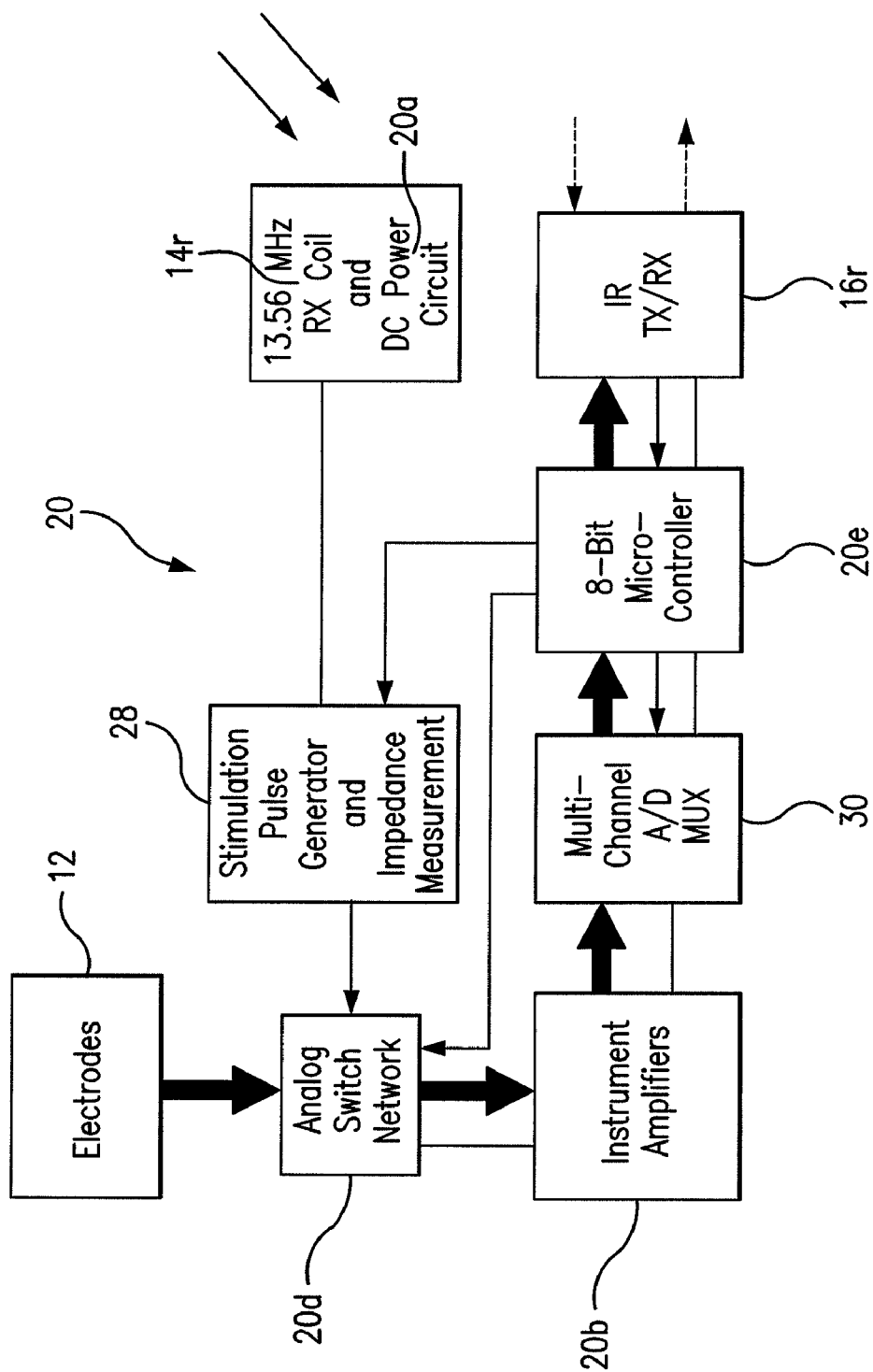
FIG. 2 is a functional block diagram of the remote circuitry and electrodes of the inventive brain-monitoring system of FIG. 1.

FIG. 2 is a functional block diagram of remote circuitry 20 and electrodes 12 of the inventive brain-monitoring system of FIG. 1. FIG. 2 illustrates the interconnectivity among the various portions of remote circuitry 20. The functional blocks in FIG. 2 are labeled, as appropriate, with reference numbers which correspond to the primary portions of remote circuitry 20 as illustrated in FIGS. 4 through 8. Electrodes 12 are connected by an analog switch network 20d (detailed in FIG. 7). Analog switch network 20d creates connections between individual electrodes and functional circuitry 28 which provides tissue stimulation current and which enables remote circuitry 20 to measure electrode impedance (detailed in FIG. 7).

An array of instrument amplifiers 20b (detailed in FIG. 5) condition the EEG signals from electrodes 12 and connect to an analog-to-digital (A/D) converter 30 which transforms the multiple analog EEG signals to digital signals in a multiplexed fashion. Under the control of a micro-controller 20e, these digital signals are transmitted to main circuitry 22 via IR transceiver 16r. Micro-controller 20e, with programmed instructions in firmware stored within micro-controller 20e, controls the functions of remote circuitry 20 and communicates with main circuitry 22.

DC power circuitry 20a to which RF inductive receive coil 14r is connected is also included in remote circuitry 20. Power circuit 20a receives transmitted power at RF frequencies from main circuitry 22 in order to power all of the elements of remote circuitry 20.

Figure 3:
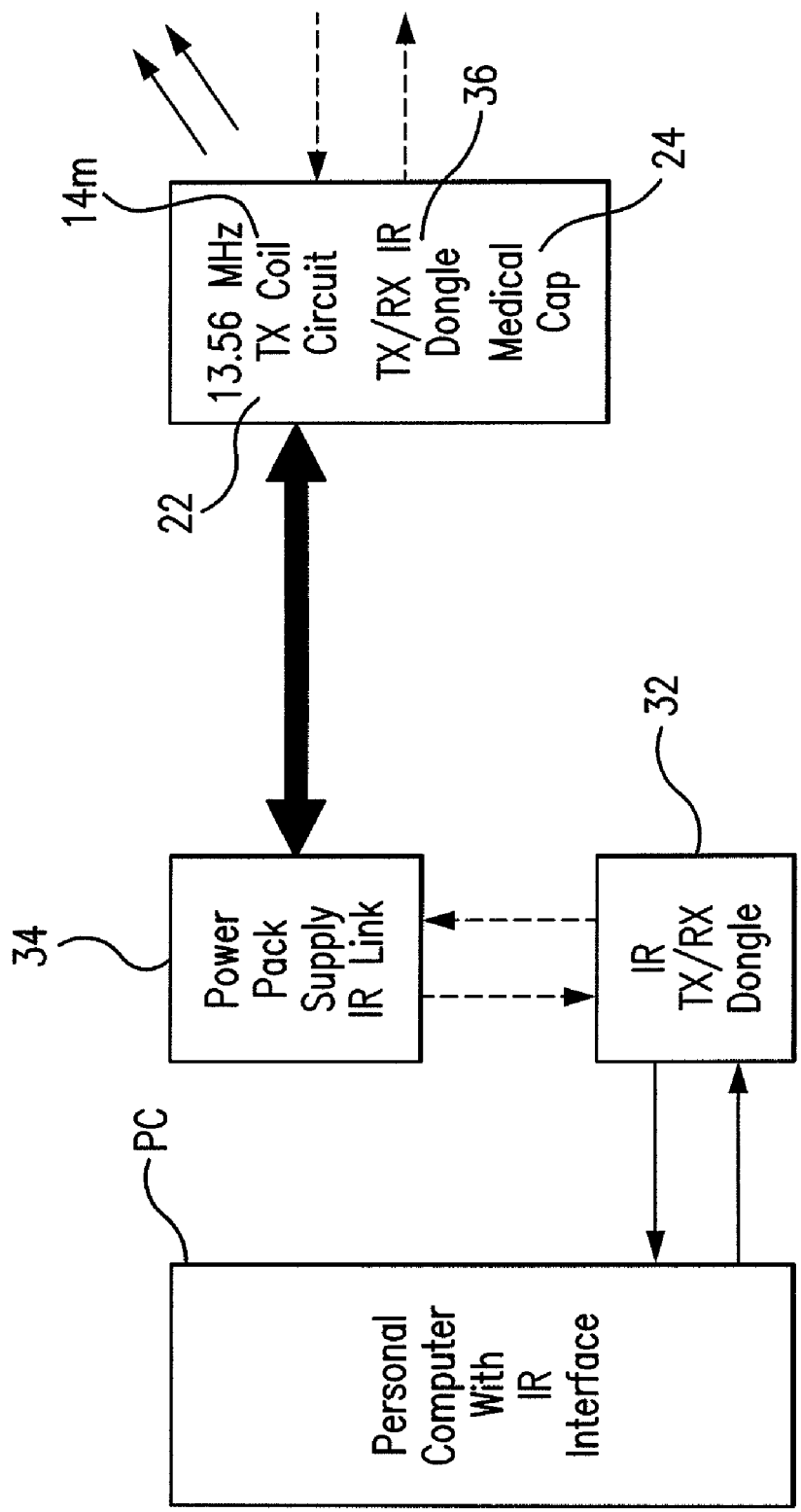
FIG. 3 is a functional block diagram including the main circuitry of the inventive brain-monitoring system of FIG. 1.

FIG. 3 is a functional block diagram including main circuitry 22 of inventive brain-monitoring system 10 of FIG. 1. Also functionally illustrated in FIG. 3 are a computer (PC) which communicates with main circuitry 22 through an IR transceiver dongle 32 which is used to communicate between the computer (PC) and main circuitry 22 when monitoring system 10 is operated without a tether. As stated above, such IR transceiver dongle devices are well-known to those skilled in the art of circuit design. An IR transceiver dongle 36 is connected to a serial port on the computer (PC) to complete the IR data link between main circuitry 22 and the computer (PC). Although IR transceivers 32 and 36 are illustrated as being positioned close to each other, there is no such limitation in the physical arrangement. IR transceivers 32 and 36 may be devices which have a range much longer than that shown in FIG. 3, thereby removing the inconvenience and interference of a tether to the computer (PC).

As stated above, details of the circuitry used to complete the data link to the computer (PC) using standard formats and protocols are well-known by those skilled in the art of circuit design and digital design and thus are not included herein. FIG. 3 also includes a functional block 34 which is a standard power supply for main circuitry 22.

FIGS. 4 and 5 through 8 are circuit diagrams of the embodiment illustrated and described generally in FIGS. 1-3. Each of these figures show a portion of remote circuitry 20 within an embodiment of inventive brain-monitoring system 10. The portions of remote circuitry 20 are interconnected as labeled in the figures, according to standard practice within the field of circuit design, illustrating the various points at which the portions of remote circuitry 20 are joined.

Remote circuitry 20 as shown in these figures has an arbitrary number (n) of electrodes, and remote circuitry 20 is shown as being expandable to provide the configuration necessary to monitor such an arbitrary number of electrodes. Larger numbers of electrodes provide greater precision in sensing certain intracranial electrical activity such as the location of epileptogenic foci to create an epileptogenic map for patient diagnosis. Many parts of remote circuitry 20 can be replicated as the number (n) of electrodes is increased, and FIGS. 5 through 8 illustrate such scaling of remote circuitry 20. For example, there is an instrument amplifier required for each of the n electrodes. In a similar fashion, depending on the number of A/D channels, switches, I/O lines, etc. in various integrated circuits, the number of such circuits required will vary depending on the value of n. Such a general situation is illustrated by the scalable portions of the circuitry in FIGS. 5 through 8. Such replication and scaling is well-known to those skilled in the art of circuit design and digital design.

In this embodiment of monitoring system 10, RF power is transmitted from main circuitry 22 to remote circuitry 20 preferably at a frequency of 13.56 MHz. This frequency is particularly well-suited to such an application since, as an FCC-designate ISM band set aside for industrial, scientific and medical devices, the band of 13.553 to 13.567 MHz (centered on 13.560 MHz) is the ISM band which has the lowest loss and least heating of body tissue. (See the *Handbook of Biological Effects of Electromagnetic Fields* by Polk and Postow, CRC Press, p. 88-91, 1991.) Biological tissue at 13.56 MHz has the lowest conductivity which means that the RF signal will penetrate the tissue to the greatest depth at this frequency.

At a frequency of 13.56 MHz, inductive receive and transmit coils such as 14r and 14m primarily create a magnetic field confined to the locality around the coil. The field diminishes rapidly with distance from the coil, much more rapidly than an electric field under the same circumstances. Thus, the fields which couple the coils are the near fields of the coil. The near field contains the propagating field, the energy storing both the electric and magnetic fields. In the near field, there is much more energy per unit volume available than in the far field; therefore, a higher degree of coupling can be achieved than in the far field alone, thereby increasing the energy transfer efficiency of the circuits.

Figure 4:
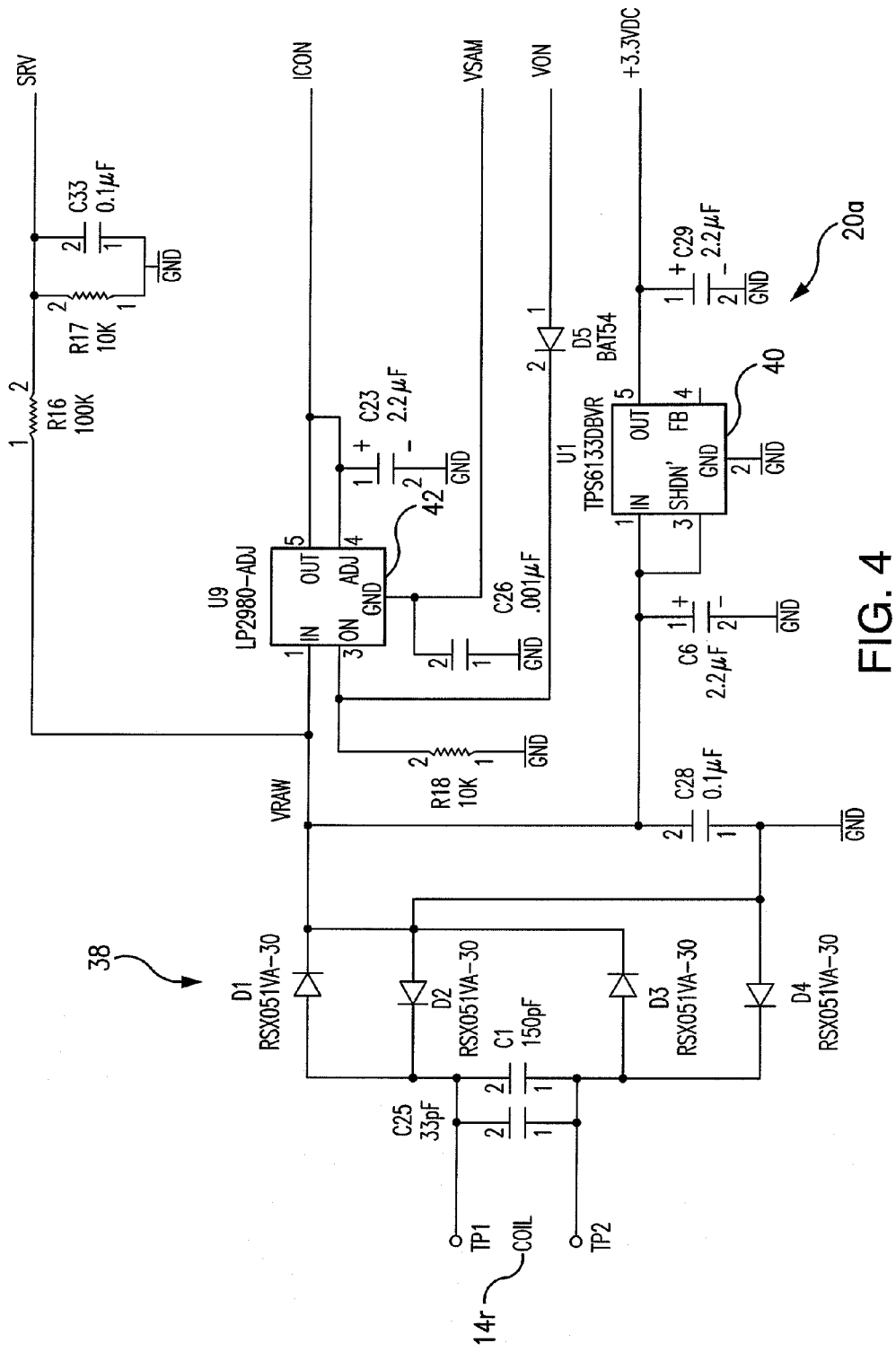
FIG. 4 is a circuit diagram of a portion of the remote circuitry of the inventive brain-monitoring system of FIG. 1, illustrating an embodiment of the power circuitry therein. This embodiment of the remote circuitry is powered exclusively by power transmitted at RF frequencies.
Figure 4A:
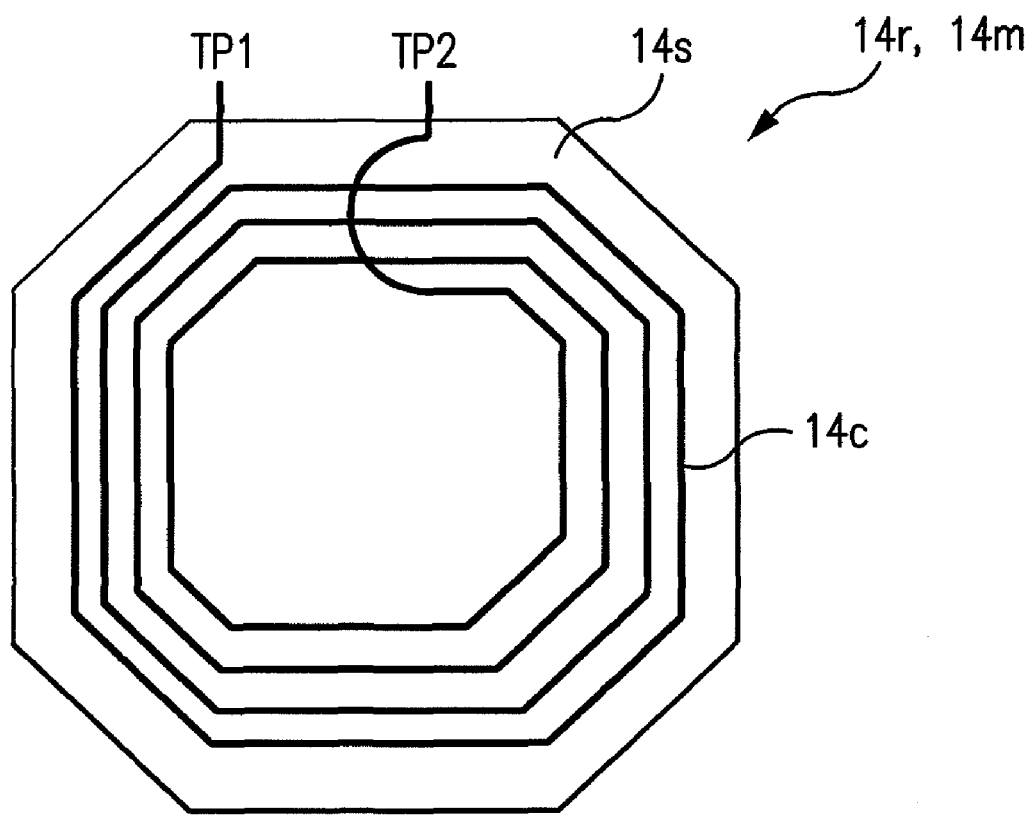
FIG. 4A is a schematic drawing of an RF inductive receive coil within the remote circuitry of the inventive brain-monitoring system of FIG. 1.

FIG. 4 is a circuit diagram illustrating an embodiment of power circuitry 20a within remote circuitry 20. RF inductive receive coil 14r receives power from main circuitry 22 through RF inductive transmit coil 14m, and this power is rectified and conditioned in portion 20a of remote circuitry 20. Four Schottky diodes 38 (also labeled as D1 through D4) are configured as a full-wave rectifier to condition the power. Diodes 38 may be Schottky barrier diodes such as diode RSX051VA-30 available from Rohm Co., Ltd. of Kyoto, Japan. The configuration of all of the components integrated into the remaining circuitry of FIG. 4 is standard and well-known to those skilled in the art of circuit design to provide clean and regulated DC power. Integrated circuit 40 is a low-dropout, low-power linear voltage regulator. Such a chip may be model TPS76133 DBVR available from Texas Instruments Inc. of Dallas, Tex. Integrated circuit 42 is an ultra-low-dropout adjustable voltage regulator. Such a chip may be model LP2980-ADJ available from National Semiconductor of Santa Clara, Calif.

FIG. 4A is a schematic drawing of an RF inductive receive coil within the remote circuitry of inventive brain-monitoring system 10 of FIG. 1. As shown, RF inductive receive coil 14r is a flexible printed circuit coil consisting of metallic conductors 14c deposited onto substrate material 14s such as Mylar film. Coil 14r is connected to power circuitry 20a at points TP1 and TP2 as shown in FIG. 4. Coil 14r is not limited to the configuration as shown in FIG. 4A. For example, coil 14r could be coiled magnet wire in a number of other coil forms. FIG. 4A is also an illustration of inductive transmit coil 14m since one embodiment of coil 14m may be essentially identical to coil 14r.

Figure 5:
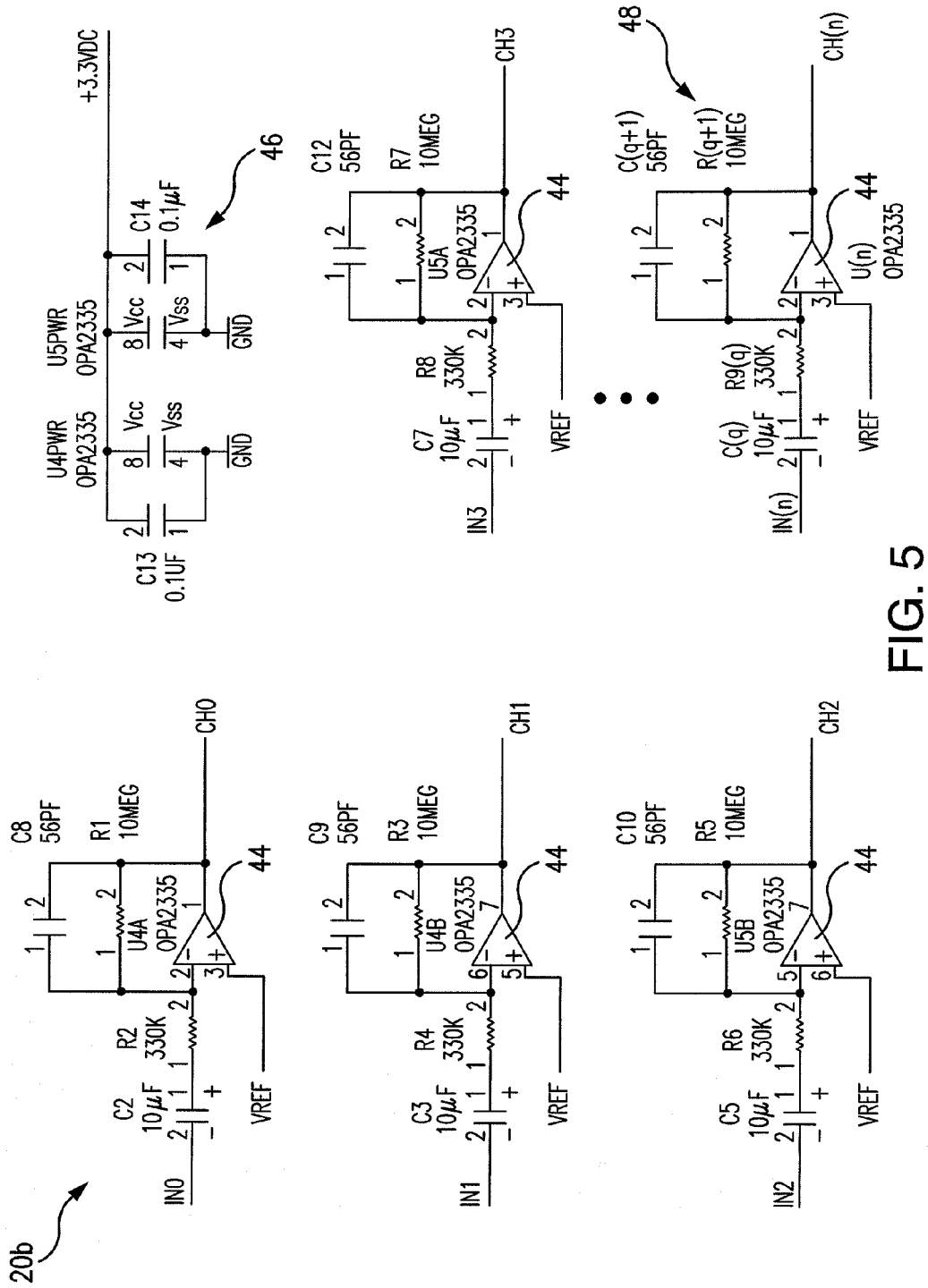
FIG. 5 is a circuit diagram of a portion of the remote circuitry of the inventive brain-monitoring system of FIG. 1, illustrating an embodiment of the instrument amplifiers therein.

FIG. 5 is a circuit diagram illustrating an embodiment of instrument amplifiers 20b within remote circuitry 20. Each electrode 12 requires an amplifier to condition the EEG signal captured thereby. As illustrated in FIG. 5, such amplifiers may be configured using CMOS operational amplifiers in a standard instrument amplifier configuration within accompanying resistors and capacitors as shown in FIG. 5. Such configurations are well-known to those skilled in the art of circuit design. Operational amplifiers 44 (several are shown) may each be one of the two amplifiers in a model OPA2335 integrated circuit CMOS dual operational amplifier chip available from Texas Instruments Inc. of Dallas, Tex. Circuit portion 46 illustrates the power connections to such multiple operational amplifiers 44.

In FIG. 5, the portion of circuitry labeled with reference number 48 illustrates the scaling of circuit portion 20b which allows for the scaling of remote circuitry according to the number (n) of electrodes 12.

Figure 6:
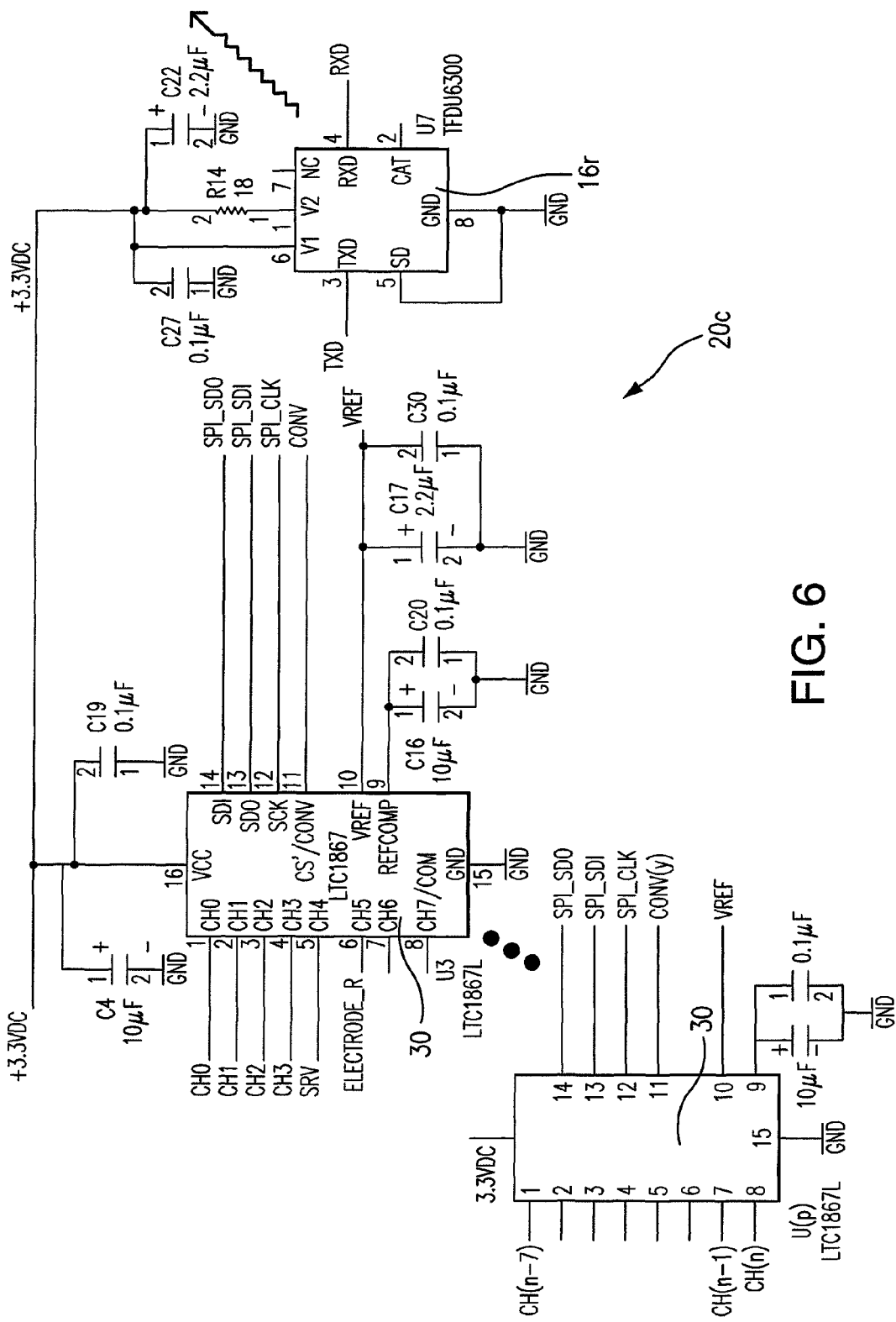
FIG. 6 is a circuit diagram of a portion of the remote circuitry of the inventive brain-monitoring system of FIG. 1, illustrating an embodiment of the A/D converter and IR transceiver therein.

FIG. 6 is a circuit diagram illustrating an embodiment of A/D converter 30 and IR transceiver 16r within remote circuitry 20. A/D converter 30 is connected to the outputs of instrument amplifiers 20b and is configured to be able to select which of the various amplifier (and therefore electrode) outputs to convert to a digital signal. Integrated circuit A/D converter 30 may be a model LTC1867L 16-bit, 8-channel A/D converter chip available from Linear Technology Corporation of Milpitas, Calif. FIG. 6 also illustrates IR transceiver 16*r* within remote circuitry 20. IR transceiver 16*r* may be a model TFDU6300 fast IR transceiver chip available from Vishay Intertechnology, Inc. of Malvern, Pa. This transceiver model has a maximum data rate of 4 Mbits per second. If the number of channels (n) increases past the point where this bandwidth is not sufficient, faster transceiver chips are available.

One very significant advantage of this inventive wireless brain-monitoring system is the separation of power and data transmission modes of communicating between remote circuitry 20 and main circuitry 22. This separation assures that the power transmission RF signal can remain at 13.56 MHz rather than being increased to accommodate data transmission in an RF band while the data bandwidth rises as the number (n) of channels grows to be very large as physicians increase the diagnostic demands on such systems.

Micro-controller 20*e* (see FIG. 8) is programmed in firmware to provide clock and control signals to A/D converter 30 that enable it to select and convert the analog signal from each channel (electrode and instrument amplifier) to a 16-bit digital signal in serial form. Each such 16-bit word is sent to micro-controller 20*e* and then forwarded to IR transceiver 16*r* for transmission to main circuitry 22. Programming of such control actions is well-known to those skilled in the art of circuit design and digital system design. IR transceiver 16*r* and micro-controller 20*e*, in a similar fashion, are configured to receive IR signals from main circuitry 22 for the control of the various functions carried out by remote circuitry 20.

As with instrument amplifiers 20*b* in FIG. 5, FIG. 6 includes circuitry to indicate that A/D conversion is scalable to accommodate an increased number of electrodes (and therefore channels) to be converted to digital signals and transmitted. Such scaling requires the addition of more A/D input channels, and FIG. 6 illustrates one approach to such scaling with the addition of another A/D converter 30 integrated circuit, as shown and labeled indicating the accommodation of n channels.

Figure 7A:
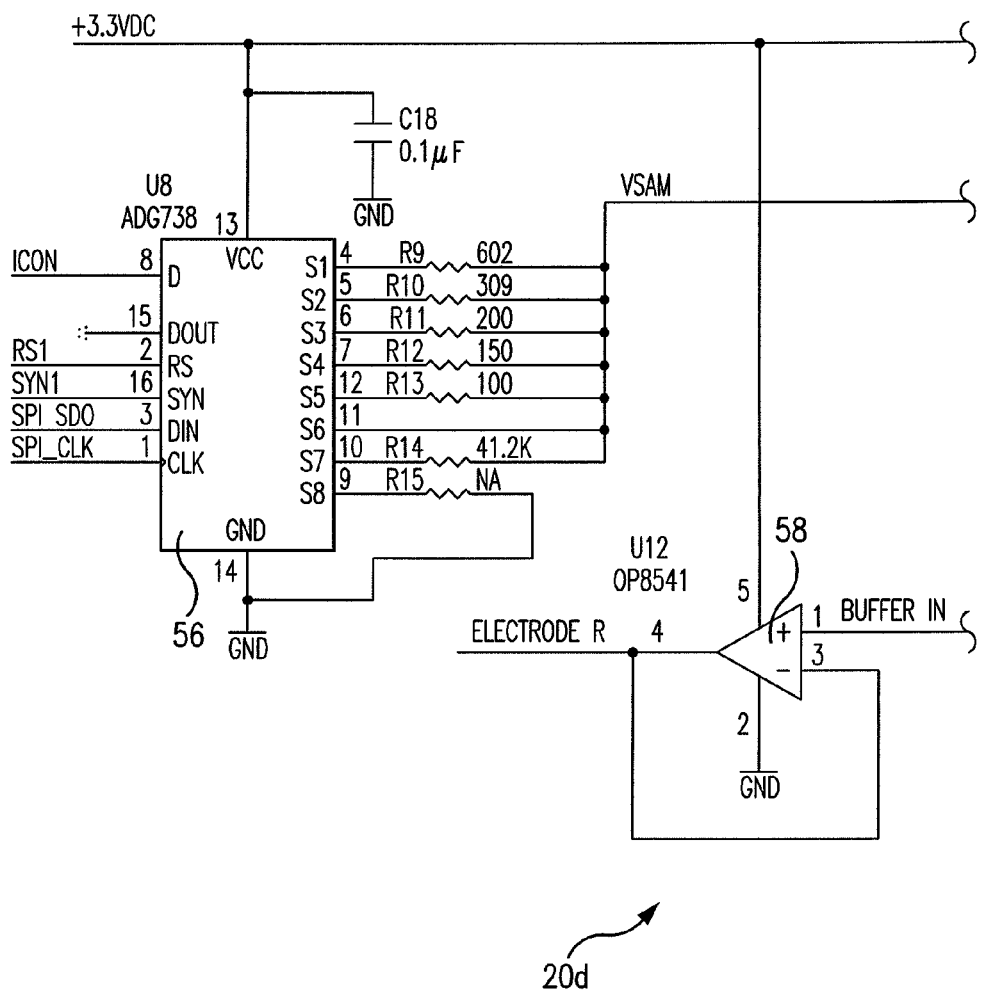
FIG. 7 is a circuit diagram of a portion of the remote circuitry of the inventive brain-monitoring system of FIG. 1, illustrating an embodiment of the analog switch network circuitry therein and including circuitry for tissue stimulation and electrode impedance measurement.
Figure 7B:
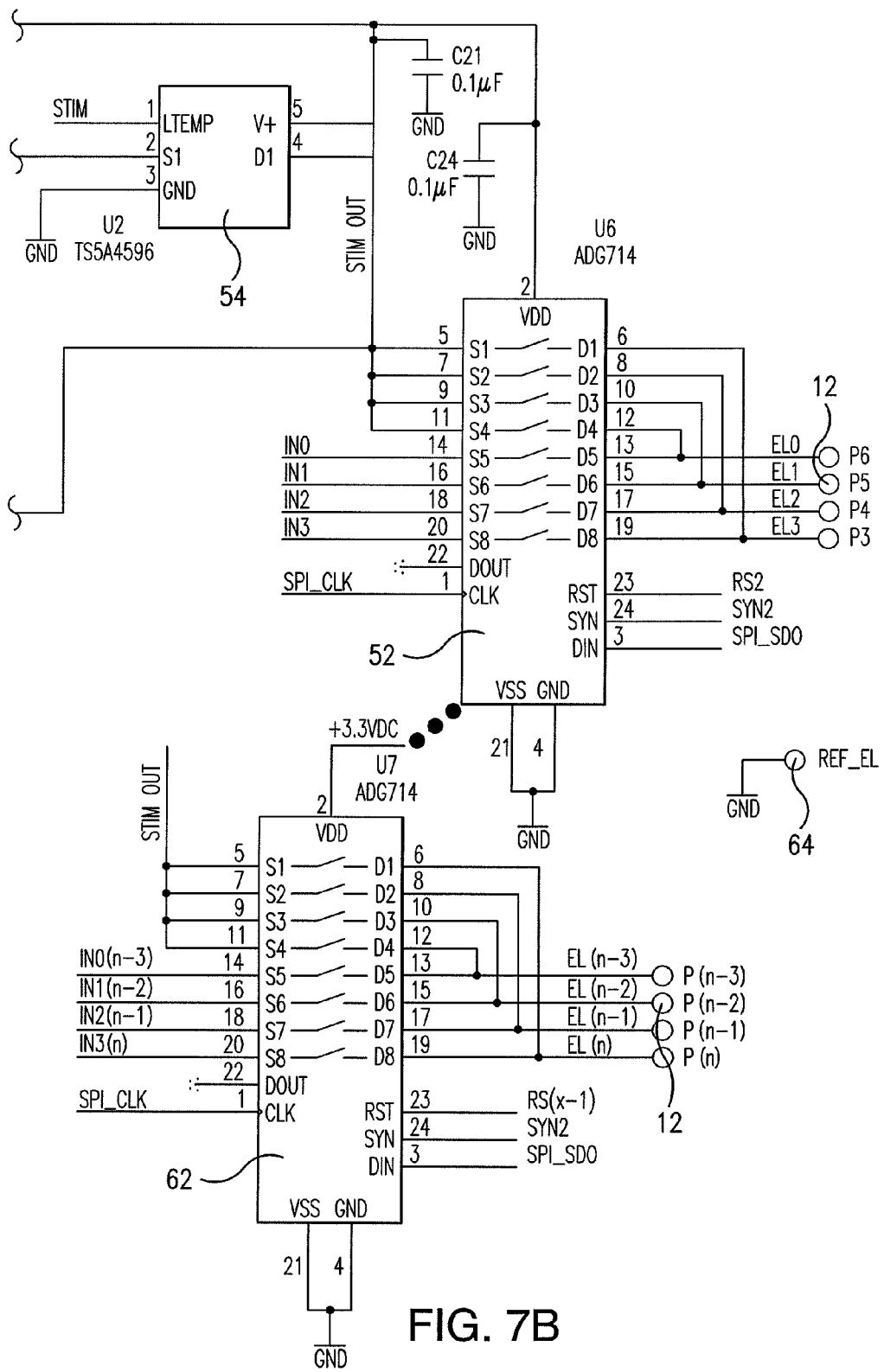

FIG. 7 is a circuit diagram illustrating an embodiment of analog switch network circuitry 20*d* including circuitry for tissue stimulation and electrode impedance measurement. This portion 20*d* of remote circuitry 20 includes multiple analog switches configured to enable each electrode 12 to be selected, under the control of programmed micro-controller 20*e*, to deliver a selected amount of electrical current to the selected electrode 12. Analog switch integrated circuit 52 is configured to select an electrode 12 for delivery of stimulation current. Analog switch 56 is configured to select the amount of stimulation current to be delivered to a selected electrode 12. In this embodiment, current values of 2, 4, 6, 8, and 10 mA are the preselected values of stimulation current, but such values should not be understood to limit the values of current to be supplied. These current values are set by selecting from among pins S1 through S5 of switch 56. Stimulation current flows through switch 54 to control the width of current pulses delivered under control of programmed micro-controller 20*e*. Typical current delivery is stream of 0.2 msec pulses delivered at a 50 Hz rate for 5 seconds, but such values are not to be understood as limiting in any way with respect to the time history, form, type, and levels of delivered stimulation current to be generated within inventive system 10.

When an electrical impedance measurement is being made, analog switch integrated circuit 56 is delivers a low-level electrical current to a selected electrode 12 for an impedance measurement. In this embodiment, the measurement is of a pair of electrodes, the selected electrode and a reference electrode 64 to complete the circuit on which the impedance measurement is taken. In this embodiment, by measuring the electrical impedance of multiple pairs of selected electrodes 12 with reference electrode 64, it will be most often possible to assess the condition of each electrode 12 over time while it is implanted in the brain.

For impedance measurements in this embodiment of remote circuitry 20, a fixed electrical current of about 50 µA is supplied at pin S7 of analog switch 56 for measurements of from 0 to about 40K ohms. A/D converter 30 is used to measure the resulting voltage (and therefore impedance) during a short pulse of the delivered low-level current. The voltage is measured on the line labeled ELECTRODE_R on which the voltage signal if buffered by a unity-gain operation amplifier 58.

Analog switch 52 may be a model ADG714 CMOS, low-voltage serially-controlled octal switch available from Analog Devices of Norwood, Mass. Analog switch 56 may be model ADG738 CMOS, low-voltage, 3-wire serially-controlled matrix switch available from Analog Devices of Norwood, Mass. Analog switch 54 may be model TS5A4596 SPST, single-channel analog switch available from Texas Instruments, Inc. of Dallas, Tex. Operational amplifier 58 may be a model AD8541 general-purpose CMOS rail-to-rail amplifier available from Analog Devices of Norwood, Mass.

As shown in several previous figures, FIG. 7 also includes circuitry to indicate the scalability of the electrode selection, stimulation and impedance measurement functions as the number (n) of electrodes 12 is increased. Analog switch integrated circuit 62 handles the representative increase in the channels to be selected.

Figure 8:
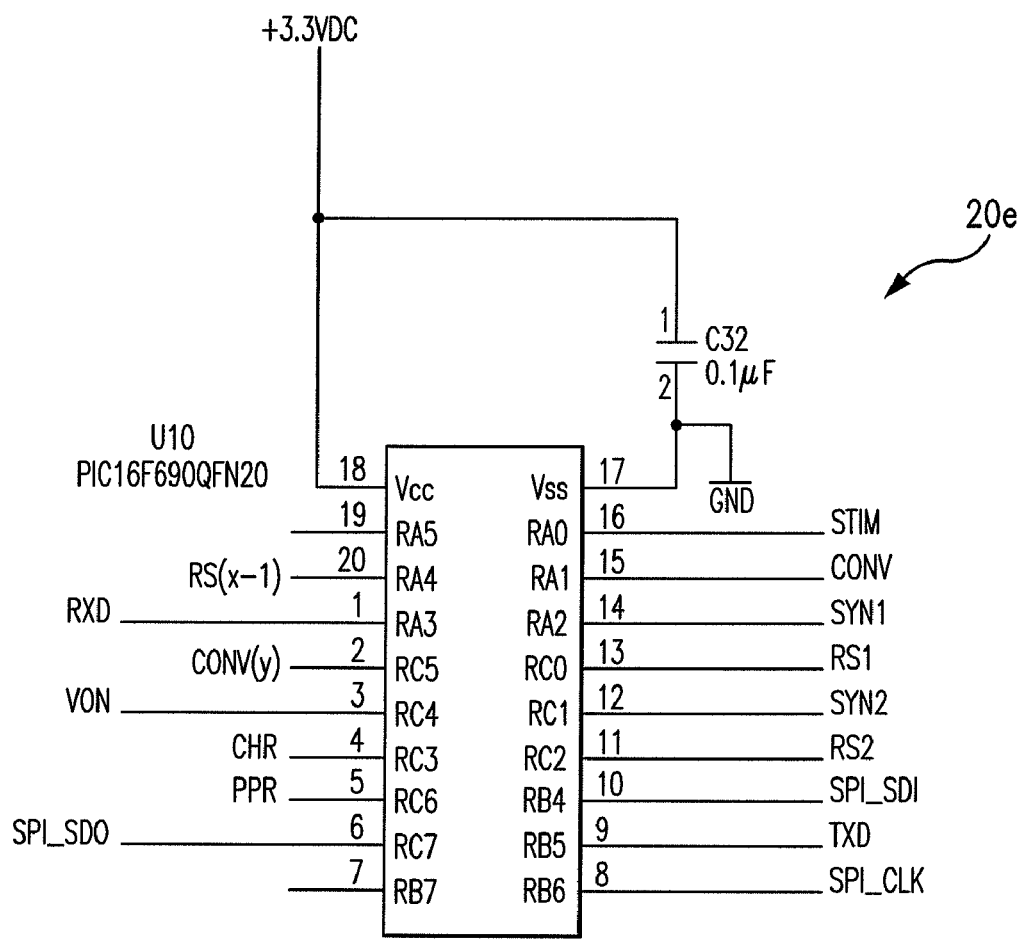
FIG. 8 is a circuit diagram of a portion of the remote circuitry of the inventive brain-monitoring system of FIG. 1, illustrating an embodiment of the micro-controller therein.

FIG. 8 is a circuit diagram illustrating an embodiment of micro-controller 20*e* within remote circuitry 20. Micro-controller 20*e* contains programmed instructions stored in firmware to carry out the functions described above. Detailed instructions are not described herein since such instructions are well-known to those skilled in the art of circuit design and digital design. As shown in FIG. 8, micro-controller 20*e* may be a model PIC16F690QFN20-pin flash-based 8-bit CMOS micro-controller available from Microchip Technology Inc. of Chandler, Ariz. Note that micro-controller 20*e* is shown with signals to control an expanded number (n) of electrodes 12. However, as n increases, a micro-controller having a sufficiently large number of I/O lines will be required to accommodate such an increase. As shown in FIG. 8, I/O lines RS(x−1), and CONV(y) accommodate additional switches and A/D converters as required.

FIG. 9 is a circuit diagram illustrating an embodiment of the RF power circuitry 22*a* within main circuitry 22. This circuitry provides 13.56 MHz RF power to be transmitted via RF inductive transmit coil 14*m* to remote circuitry 20. An oscillator chip 68 generates the 13.56 MHz signal, and a non-inverting buffer amplifier 66 provides the drive current for a class-D amplifier 72. A linear regulator 70 provides the 5VDC power required by oscillator chip 68 and buffer amplifier 66.

Buffer amplifier 66 may be a model 74HC541 non-inverting buffer integrated circuit available from Texas Instruments Inc. of Dallas, Tex. Oscillator chip 68 may be a model ECS-P53-13.56-A programmable SMD clock oscillator available from ECS Inc. International of Olathe, Kans. Linear regulator 70 may be a model MAX1598 low-dropout linear regulator available from Maxim Integrated Products, Inc. of Sunnyvale, Calif. Amplifier 72 may be a model ZVN4310G DMOS FET available from Zetex Semiconductors plc of Chadderton, Oldham, United Kingdom. Inductor $L_1$ may be a 3-turn air coil of 22-gauge magnet wire with an inside diameter of 0.187 inches.

Figure 9A:
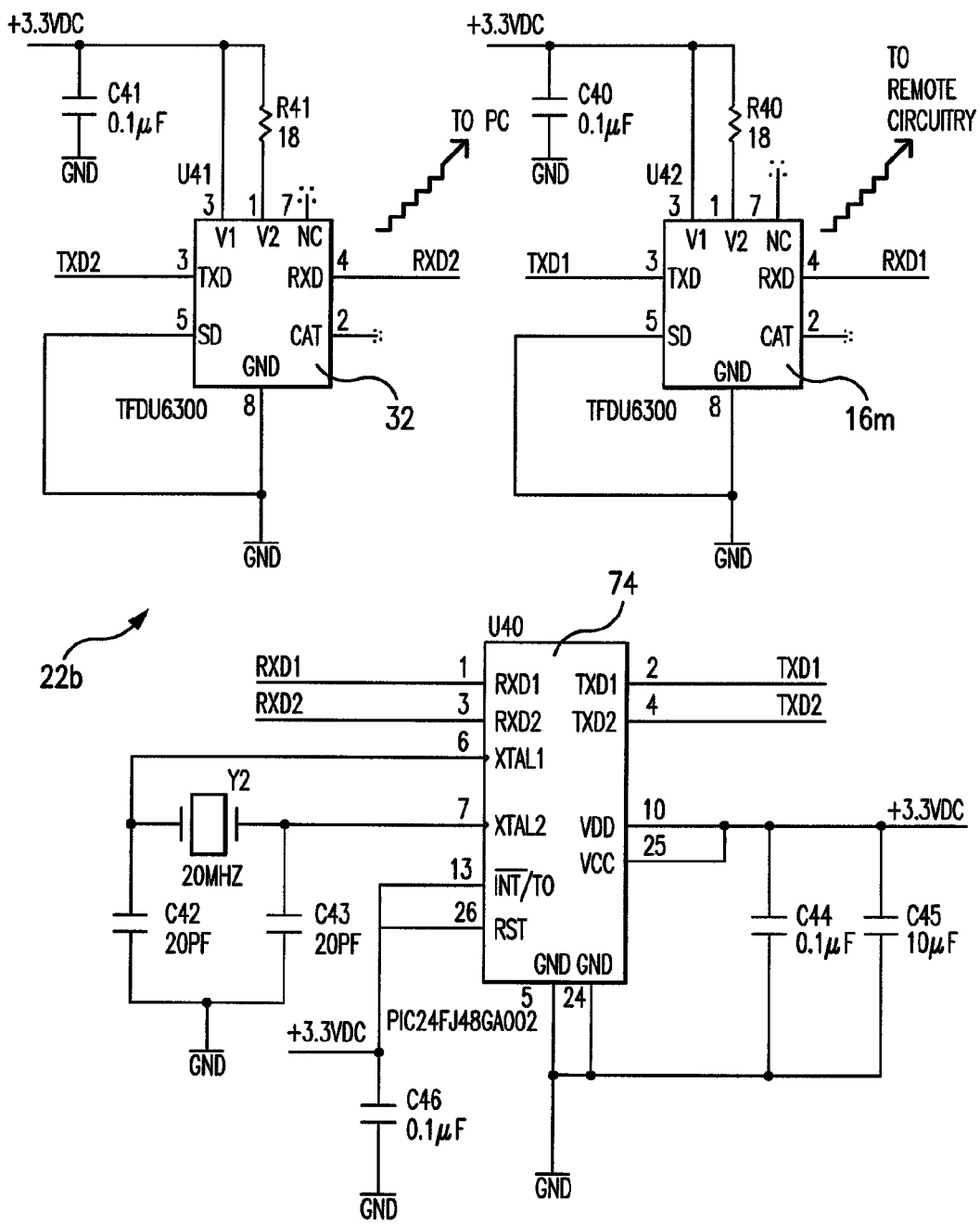
FIG. 9A is a circuit diagram of a portion of the main circuitry of the inventive brain-monitoring system of FIG. 1, illustrating an embodiment of the infrared data link to the remote circuitry.

FIG. 9A is a circuit diagram of the data transmission portion 22b of main circuitry 22 of the inventive brain-monitoring system of FIG. 1, illustrating an embodiment of the infrared data link to remote circuitry 20. FIG. 9A also illustrates an infrared data link to the computer (PC) which communicates with main circuitry 22 over another such data link. Two IR transceiver integrated circuits 16m and 32 are shown. IR transceiver 16m communicates with remote circuitry 20, and IR transceiver 32 communicates with the computer (PC) as is illustrated in FIGS. 1 and 3. Data transmission circuitry 22b also includes a micro-controller 74, including stored firmware instructions, which controls the functions of IR transceivers 16m and 32. Such firmware instructions are well-known to those skilled in the art of digital design and are not discussed in further detail herein. The interconnections necessary to carry out such functions are shown in FIG. 9A.

IR transceivers 16m and 32 may be the same integrated circuits as IR transceiver 16r. Micro-controller 74 may be a model PIC2444FJ48GA002 16-bit micro-controller available from Microchip Technology Inc. of Chandler, Ariz.

Figure 10A:
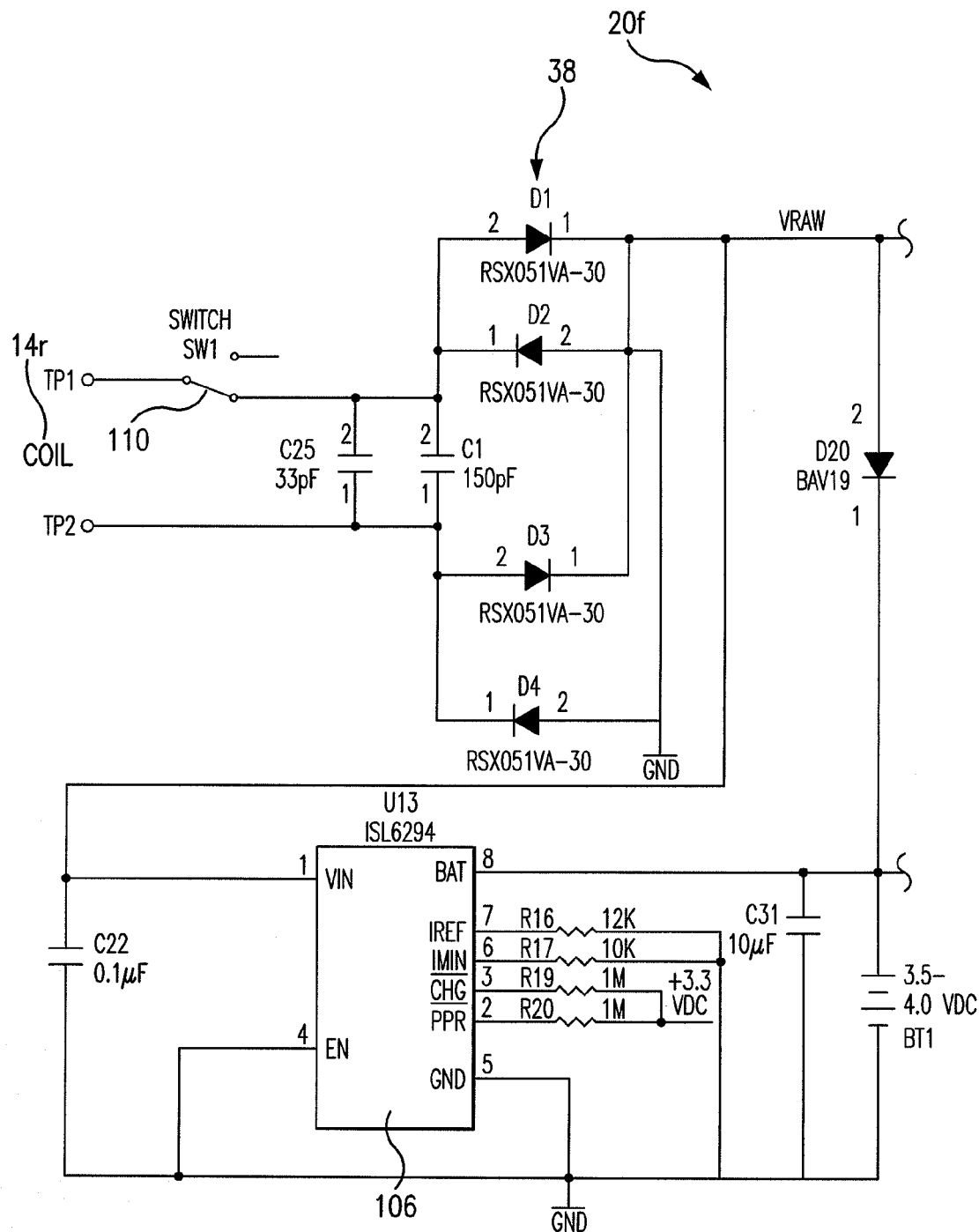
FIG. 10 is a circuit diagram of a portion of the remote circuitry of the inventive brain-monitoring system of FIG. 1, illustrating an alternative embodiment of the power circuitry therein including a solid-state lithium rechargeable battery and power capacitor.
Figure 10B:
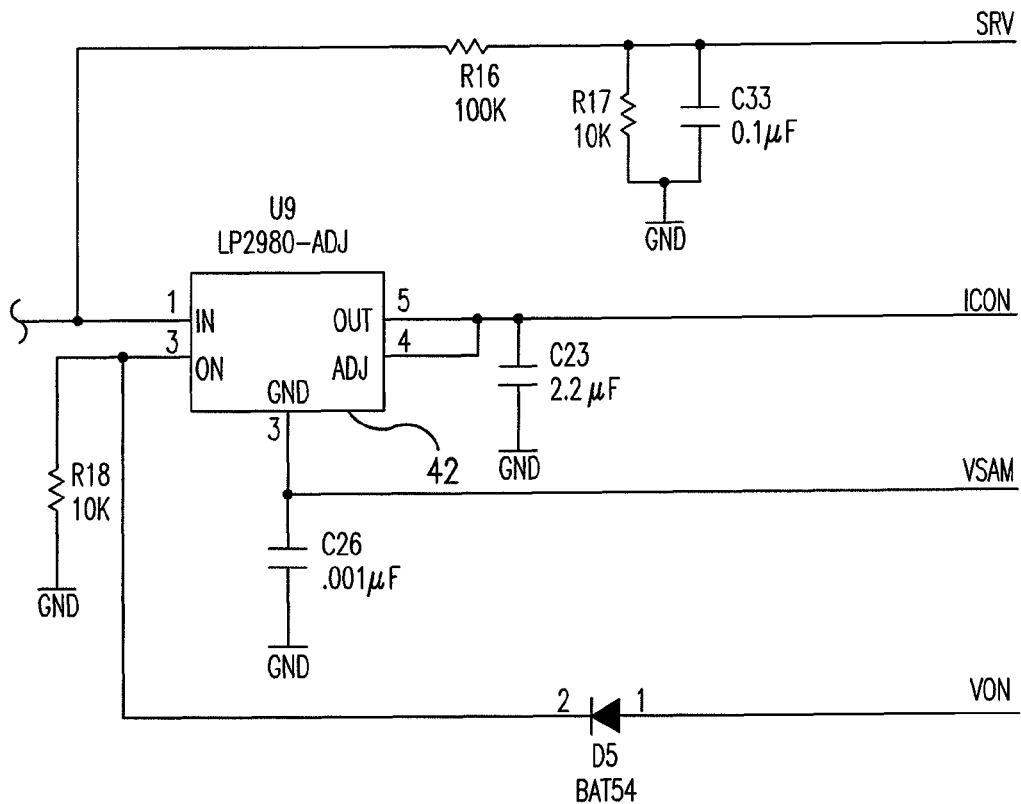
Figure 10B:
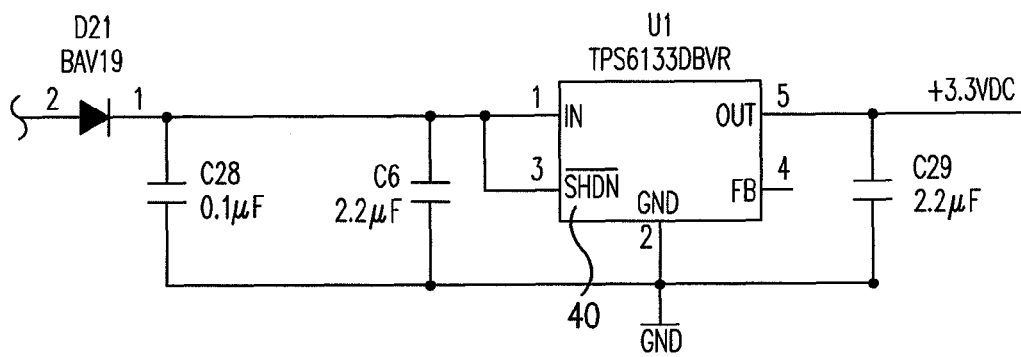

FIG. 10 is a circuit diagram of a portion 20f of the remote circuitry 20 of the inventive brain-monitoring system of FIG. 1, illustrating an alternative embodiment of the power circuitry including a solid-state lithium rechargeable battery BT1. Portion 20f of remote circuitry 20, in addition to solid-state lithium rechargeable battery BT1, includes a power capacitor C31 and a single-cell Li-ion battery charger integrated circuit 106. Four Schottky diodes 38 (also labeled as D1-D4) are configured as a full-wave rectifier to condition the power as in portion 20a in FIG. 4. The configuration of all of these components integrated into the remaining circuitry of FIG. 10 is standard and well-known to those skilled in the art of circuit design. Battery charger integrated circuit 106 may be a model ISL6294 integrated circuit available from Intersil Corporation of Milpitas, Calif.

Battery BT1 may be a flexible, thin-film battery such as is available from ITN Energy Systems of Littleton, Colo. Such solid-state lithium rechargeable batteries utilize stable, safe, reversible chemistry and have a high power density. Also, batteries of this type can be cycled more than 10,000 times and have a long shelf life. As a solid-state (dry) component, such a battery is ideal for use in a medical implant. The physical configuration of such a battery is also ideal for miniaturization within an implant device.

Power capacitor C31 is positioned to store charge across battery BT1 such that if remote circuitry 20 should require a higher current for short periods of time than can be provided by the RF transmission source or battery BT1, capacitor C31 in a charged state can meet such current demand.

Steering diodes 112 and 114 (also labeled D20 and D21, respectively) allow power to flow from the higher voltage of the two sources, battery BT1 and power capacitor C31 or voltage VRAW provided by RF power transmission. VRAW also provides power to the charging circuit.

Remote circuitry 20 may be configured with either power capacitor C31 or battery BT1 (and related charging circuitry) or both as illustrated in FIG. 10. Depending on these alternatives, remote circuitry 20 is configured in standard ways as are well known by those skilled in the state-of-the-art of circuit design.

FIG. 10 also illustrates a switch 110 which serves as a circuit-loop-interrupting element. Switch 110 may be a miniature mechanically-actuated switch which is positioned to be actuated through the skin. Switch 110 is placed in its OPEN position when it is necessary to expose the patient being monitored into an MRI environment. Actuation of switch 110 back into its CLOSED state is carried out in a similar fashion. As illustrated in FIG. 10, switch 110 interrupts a circuit loop formed by coil 14r (not shown in FIG. 10) connected between points TP1 and TP2. Opening such a circuit loop reduces the effect of induced electrical currents in remote circuitry 20.

FIG. 11 is a schematic illustration of a possible physical configuration showing the inclusion of battery 122 (identified as BT1 in FIG. 10) in the packaging of remote circuitry 20 within the alternative embodiment of FIG. 10. FIG. 11 is highly schematic in that the integrated circuits IC1-IC4 shown on the circuit board 120 are only representative and do not correspond to particular integrated circuits within remote circuitry 20 shown in FIG. 10. Battery 122 is shown as a thin-film component mounted on one side of a circuit board 120 on which remote circuitry 20 has been placed.

A video camera may be aimed at the patient during monitoring and mapping using wireless system 10. A video camera (not shown) typically generates a stream of time stamps to identify precisely the time at which a video frame is captured. Wireless system 10 can be synchronized with the video stream from the camera by synchronizing the digital stream of data being transmitted from remote circuitry 20. One possibility is to create a synchronizing time mark in the data stream from remote circuitry 20 by triggering a single stimulation event at a known video time stamp. Subsequent analysis of the data stream from remote circuitry 20 can be done with precise knowledge of the related video imagery.

It is desirable to package remote circuitry 20 in as small a package as possible. Accordingly, remote circuitry 20 may be produced using ASIC technology (application-specific integrated circuits), integrated circuits which achieve a high degree of integration and size reduction. Remote circuitry 20 as illustrated in the embodiments of FIGS. 4, 5 through 8, and 10 is shown as being constructed using discrete components, but such illustration is only for purposes of explanation and should not be taken as limiting in any way as to how remote circuitry 20 should be physically configured. It should be noted that either with discrete integrated circuits or with an ASIC, very low power devices may be used to keep the power consumption as low as possible in remote circuitry 20.

While the principles of this invention have been described in connection with specific embodiments, it should be understood clearly that these descriptions are made only by way of example and are not intended to limit the scope of the invention.

The invention claimed is:

1. A wireless system for brain monitoring/mapping of neurological-disorder patients, the system comprising:

a plurality of electrodes each configured for surface abutment of brain tissue;

main circuitry configured to be placed outside a body of a patient, the main circuitry including a cable with an RF inductive transmit coil and a IR transceiver located at an end thereof, the RF inductive transmit coil and the IR transceiver being held by a cap such that they are positioned and configured to transmit power at radio frequencies and send and receive data using infrared energy; and remote circuitry configured to be subcutaneously implanted in a head of the patient, the remote circuitry including an RF inductive receiving coil and an IR transceiver, the remote circuitry being connected to the plurality of electrodes and configured to (a) receive transmitted power at radio frequencies from the main circuitry, (b) capture and digitize full-bandwidth EEG signals from each of the electrodes, and (c) send data to and receive data from the main circuitry using infrared energy, including sending the digitized full-bandwidth EEG signals from each of the electrodes.

2. The wireless neurological-disorder monitoring/mapping system of claim 1 wherein the remote circuitry is further configured to measure electrical impedance of each of the plurality of electrodes.

3. The wireless neurological-disorder monitoring/mapping system of claim 2 wherein the remote circuitry is further configured to send the measurements of the electrical impedance to the main circuitry as digital signals.

4. The wireless neurological-disorder monitoring/mapping system of claim 1 wherein each of the plurality of electrodes is a flat contact within a flexible grid of flat contacts or a depth probe.

5. The wireless neurological-disorder monitoring/mapping system of claim 1 wherein the radio frequencies are in a range of between 13.55 MHz and 13.57 MHz.

6. The wireless neurological-disorder monitoring/mapping system of claim 1 wherein each digital signal has a digital resolution of at least about 12-16 bits.

7. The wireless neurological-disorder monitoring/mapping system of claim 1 wherein sampling occurs at least about 500 times per second.

8. The wireless neurological-disorder monitoring/mapping system of claim 1 wherein the remote circuitry further includes a power storage capacitor, whereby the capacitor provides power when high current flow is required.

9. The wireless neurological-disorder monitoring/mapping system of claim 1 wherein the remote circuitry further includes a battery to augment the RF-supplied power.

10. The wireless neurological-disorder monitoring/mapping system of claim 9 wherein the battery is a solid-state lithium rechargeable battery.

11. The wireless neurological-disorder monitoring/mapping system of claim 9 wherein the remote circuitry further includes a power storage capacitor, whereby the capacitor provides power when high current flow is required.

12. The wireless neurological-disorder monitoring/mapping system of claim 1 wherein the remote circuitry further includes at least one circuit-loop-interrupting element having an open state, thereby rendering the remote circuit MRI-safe when the at least one circuit-loop-interrupting element is in the open state.

13. The wireless neurological-disorder monitoring/mapping system of claim 1 further including a video camera and recording system to synchronously record the full-bandwidth EEG signals and video images of the patient.

14. The wireless neurological-disorder monitoring/mapping system of claim 1 wherein the remote circuitry is further configured to provide electrical energy to at least one of the plurality of electrodes to stimulate brain tissue.

15. The wireless neurological-disorder monitoring/mapping system of claim 14 wherein the remote circuitry is further configured to measure electrical impedance of each of the plurality of electrodes.

16. The wireless neurological-disorder monitoring/mapping system of claim 15 wherein the remote circuitry is further configured to send the measurements of the electrical impedance to the main circuitry as digital signals.

17. The wireless neurological-disorder monitoring/mapping system of claim 15 wherein each of the plurality of electrodes is a flat contact within a flexible grid of flat contacts or a depth probe.

18. The wireless neurological-disorder monitoring/mapping system of claim 14 wherein the radio frequencies are in a range of between 13.55 MHz and 13.57 MHz.

19. The wireless neurological-disorder monitoring/mapping system of claim 14 wherein each digital signal has a digital resolution of at least about 12-16 bits.

20. The wireless neurological-disorder monitoring/mapping system of claim 14 wherein sampling occurs at least about 500 times per second.

21. The wireless neurological-disorder monitoring/mapping system of claim 14 wherein the remote circuitry further includes a power storage capacitor, whereby the capacitor provides power when high current flow is required.

22. The wireless neurological-disorder monitoring/mapping system of claim 14 wherein the remote circuitry further includes a battery to augment the RF-supplied power.

23. The wireless neurological-disorder monitoring/mapping system of claim 22 wherein the battery is a solid-state lithium rechargeable battery.

24. The wireless neurological-disorder monitoring/mapping system of claim 22 wherein the remote circuitry further includes a power storage capacitor, whereby the capacitor provides power when high current flow is required.

25. A wireless system for brain monitoring/mapping of epilepsy patients, the system comprising:
    a plurality of electrodes each configured for surface abutment of brain tissue;
    main circuitry configured to be placed outside a body of a patient, the main circuitry including a cable with an RF inductive transmit coil and a IR transceiver located at an end thereof, the RF inductive transmit coil and the IR transceiver being held by a cap such that they are positioned and configured to transmit power at radio frequencies and send and receive data using infrared energy; and
    remote circuitry configured to be subcutaneously implanted in a head of the patient, the remote circuitry including an RF inductive receiving coil and an IR transceiver, the remote circuitry being connected to the plurality of electrodes and configured to (a) receive transmitted power at radio frequencies from the main circuitry, (b) capture and digitize full-bandwidth EEG signals from each of the electrodes, and (c) send data to and receive data from the main circuitry using infrared energy, including sending the digitized full-bandwidth EEG signals from each of the electrodes.

26. The wireless epilepsy monitoring/mapping system of claim 25 wherein the remote circuitry is further configured to measure the electrical impedance of each of the plurality of electrodes.

27. The wireless epilepsy monitoring/mapping system of claim 26 wherein the remote circuitry is further configured to send the impedance measurements to the main circuitry as digital signals.

28. The wireless epilepsy monitoring/mapping system of claim 25 wherein each of the plurality of electrodes is a flat contact within a flexible grid of flat contacts or a depth probe.

29. The wireless epilepsy monitoring/mapping system of claim 25 wherein the circuitry is further configured to provide electrical energy to at least one of the plurality of electrodes to stimulate brain tissue.

* * * * *